United States Patent
Dury et al.

(10) Patent No.: US 8,263,803 B2
(45) Date of Patent: Sep. 11, 2012

(54) PREPARATION OF METALLIC DIHYDROXYBENZENE-DISULFONATES

(75) Inventors: Michel Dury, Lyons (FR); Hervé Bres, Chaponost (FR)

(73) Assignee: Rhodia Operations, Aubervilliers (FR)

( * ) Notice: Subject to any disclaimer, the term of this patent is extended or adjusted under 35 U.S.C. 154(b) by 459 days.

(21) Appl. No.: 12/304,887

(22) PCT Filed: Jun. 12, 2007

(86) PCT No.: PCT/EP2007/055758
§ 371 (c)(1),
(2), (4) Date: Nov. 17, 2009

(87) PCT Pub. No.: WO2007/144344
PCT Pub. Date: Dec. 21, 2007

(65) Prior Publication Data
US 2010/0056823 A1    Mar. 4, 2010

(30) Foreign Application Priority Data

Jun. 13, 2006  (FR) ..................................... 06 05242

(51) Int. Cl.
*C07C 309/42*    (2006.01)

(52) U.S. Cl. ........................................ 562/115; 562/123
(58) Field of Classification Search .................. 562/115, 562/123
See application file for complete search history.

(56) References Cited

U.S. PATENT DOCUMENTS 3,547,988 A    12/1970    Bean et al.
3,772,379 A    11/1973    Woodgate et al.

FOREIGN PATENT DOCUMENTS

WO    WO 99/54292    10/1999

OTHER PUBLICATIONS

International Search Report corresponding to PCT/EP 2007/0055758 issued on Aug. 23, 2007.

*Primary Examiner* — Peter G O Sullivan
(74) *Attorney, Agent, or Firm* — SNR Denton US LLP

(57) ABSTRACT

Metallic dihydroxybenzenedisulfonates are prepared, preferably from alkaline metals, from corresponding dihydroxybenzenedisulfonic acids, by reacting the dihydroxybenzenedisulfonic acid present in a sulfuric medium with an adequate amount of a salt including a sulfate or hydrogenosulfate anion.

28 Claims, No Drawings

PREPARATION OF METALLIC DIHYDROXYBENZENE-DISULFONATES

CROSS-REFERENCE TO PRIORITY/PCT APPLICATIONS

This application claims priority under 35 U.S.C. §119 of FR 0605242, filed Jun. 13, 2006, and is a continuation/national phase of PCT/EP 2007/055758, filed Jun. 12, 2007 and designating the United States (published in the French language on Dec. 21, 2007, as WO 2007/144344 A1; the title and abstract were also published in English), each hereby expressly incorporated by reference in its entirety and each assigned to the assignee hereof.

The subject matter of the present invention is a process for the preparation of metal dihydroxybenzenedisulfonates from corresponding dihydroxybenzenedisulfonic acids.

The invention is targeted more particularly at alkali metal salts, preferably the sodium or potassium salts.

The salts of dihydroxybenzenedisulfonic acids, in particular sodium 1,2-dihydroxy-3,5-benzenedisulfonate monohydrate, have applications in many fields, in particular that of photography, of water treatment and of detergency.

The preparation of metal dihydroxybenzenedisulfonates, in particular the sodium salts, is described in the literature.

Thus, according to U.S. Pat. No. 3,772,379, it is known to prepare said salts according to a process which comprises the following stages:
dissolution of the dihydroxybenzene (diphenol) in sulfuric acid;
addition of fuming sulfuric acid, resulting in a highly acidic medium, the amount of sulfuric acid being sufficient to produce said disulfonate;
heating the medium at between approximately 60° C. and 90° C.;
diluting the reaction medium by addition of water;
reaction of said medium with an alkali metal hydroxide, the amount of alkali metal hydroxide being sufficient to produce the alkali metal dihydroxybenzenedisulfonate in the precipitated form;
heating the medium in order to hydrolyze any sulfuric ester.

Similarly, the sulfonation of the dihydroxybenzene can be carried out using oleum.

In the sulfonation process, the sulfuric acid is always employed in an excess amount and it is therefore important to recover it.

In point of fact, in the process described, an aqueous alkali metal hydroxide, in particular sodium hydroxide, solution is involved in carrying out the salification of the dihydroxybenzenedisulfonic acid.

After separation of the sodium dihydroxybenzenedisulfonate by filtration, a filtrate (mother liquors) is obtained which comprises recoverable sulfuric acid but which occurs diluted as a result of sodium hydroxide being supplied in the form of an aqueous solution and as a result of the salification reaction with sodium hydroxide resulting in the formation of water.

Similarly, U.S. Pat. No. 3,547,988 describes that the salification is carried out using an alkali metal base or ammonium base and that alkali metal hydroxides are preferred.

In order to overcome these disadvantages, the present invention provides a process which makes it possible to more easily regenerate the mother liquors comprising sulfuric acid resulting from the separation of the metal dihydroxybenzenedisulfonate.

The subject matter of the present invention is a process for the preparation of a metal dihydroxybenzenedisulfonate from a corresponding dihydroxybenzenedisulfonic acid, characterized in that it comprises the reaction of the dihydroxybenzenedisulfonic acid, present in a sulfuric medium, with a sufficient amount of a salt comprising a sulfate or hydrogen sulfate anion.

According to a preferred alternative embodiment of the process of the invention, the salification operation according to the invention is carried out on the reaction medium resulting from the preliminary sulfonation stage.

It has been found that it is possible to prepare the salts of the dihydroxybenzenedisulfonic acid by salification of the dihydroxybenzenedisulfonic acid using a metal sulfate or hydrogen sulfate, preferably sodium or potassium sulfate or hydrogen sulfate, without detrimentally affecting the quality of the final compound.

The use of a salification agent of sulfate or hydrogen sulfate type does not release water during the salification reaction.

Thus, without, however, relating the scope of the invention to the reaction mechanisms, the process of the invention is illustrated by the following reactions, applied to the preferred substrates of the invention:

or

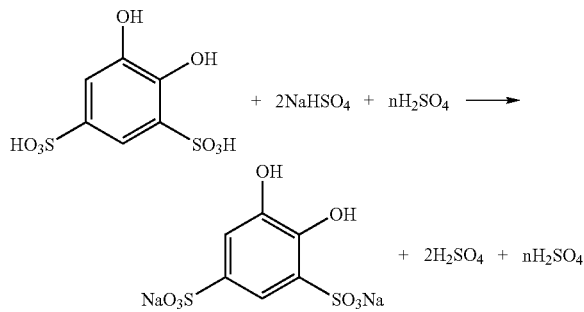

This type of salification, which is a neutralization of the two sulfonic acid functional groups by a sulfate or hydrogen sulfate salt, makes it possible to form sulfuric acid during this reaction and thus, after separation (generally by filtration) of the expected salt from the reaction medium, to more easily regenerate the mother liquors comprising the sulfuric acid.

The mother liquors resulting from the separation are concentrated in sulfuric acid (>60%) and can be directly conveyed to the regeneration, thus rendering this process devoid of aqueous effluent.

The process of the invention applies to any dihydroxybenzenedisulfonic acid.

It can be symbolized in particular by the following formula:

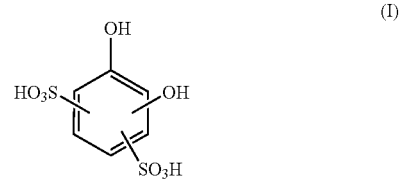

in said formula:
the OH group being in the ortho, meta or para position with respect to the other hydroxyl group, the sulfonic $SO_3H$ groups being in the ortho and/or para position with respect to the hydroxyl groups.

The invention does not exclude the presence of one or two substituents on the benzene ring insofar as they do not interfere.

Mention may be made, as more specific examples, inter alia, of linear or branched alkyl or alkoxy groups having from 1 to 20 carbon atoms, preferably from 1 to 6 carbon atoms; perfluoroalkyl groups having from 1 to 4 carbon atoms; or halogen atoms, preferably chlorine, bromine or fluorine.

Mention may be made, as preferred examples of dihydroxybenzenedisulfonic acids employed, of the disulfonic acids resulting from the sulfonation of hydroquinone (1,4-dihydroxybenzene), of pyrocatechol (1,2-dihydroxybenzene) and of resorcinol (1,3-dihydroxybenzene).

The preferred dihydroxybenzenedisulfonic acids are 1,2-dihydroxy-3,5-benzenedisulfonic acid, 1,3-dihydroxy-4,6-benzenedisulfonic acid or 1,4-dihydroxy-2,5-benzenedisulfonic acid.

In accordance with the process of the invention, the dihydroxybenzenedisulfonic acid is reacted with a salt comprising a sulfate or hydrogen sulfate anion.

In order to simplify the account, said salt will be denoted subsequently "sulfate or hydrogen sulfate".

The sulfate or hydrogen sulfate anion can be involved in any form.

The requirement which governs the choice of the salt is that the salt has to be basic in nature so that it is soluble in the reaction medium.

A metal element and more particularly an element from Group Ia or Ib of the Periodic Table of the Elements may be involved.

For the definition of the elements, reference is made below to the Periodic Table of the Elements published in the Bulletin de la Société Chimique de France, No. 1 (1966).

Mention may be made, as metal elements of Group Ia, of lithium, sodium and potassium and, as metal elements of Group Ib, of copper and silver.

However, for economic reasons, it is preferable to have recourse to readily accessible commercial forms.

The choice is advantageously made of a metal element of alkali metal type belonging to Group Ia.

Sodium, potassium or lithium sulfate or hydrogen sulfate is preferably involved.

Sodium sulfate or potassium sulfate is very particularly chosen.

The sulfate or hydrogen sulfate salt is preferably employed in the solid form in order not to dilute the reaction medium.

The amount of sulfate or hydrogen sulfate salt employed, expressed by the ratio of the number of moles of sulfate or hydrogen sulfate salt to the number of moles of dihydroxybenzenedisulfonic acid, varies between 1.6 and 2.5, preferably between 1.9 and 2.1, and is preferably in the vicinity of 2.0. Use is thus made of an amount of corresponding salt preferably equal to the stoichiometry of the reaction (ratio of 2) or close to the stoichiometry as defined in the abovementioned range.

From a practical viewpoint, the sulfate or hydrogen sulfate salt is introduced into the reaction medium comprising the dihydroxybenzenedisulfonic acid or vice versa.

The salification reaction is carried out at a temperature of between 40° C. and 80° C., preferably between 50° C. and 60° C.

The dihydroxybenzenedisulfonic acid is then in the salified form, preferably in the sodium or potassium salt form when the salt chosen is sodium or potassium sulfate or hydrogen sulfate. It can be in the hydrated form, generally in the monohydrate form.

It precipitates from the reaction medium.

After returning to ambient temperature between 15° C. and 30° C., the precipitate is separated according to conventional solid/liquid separation techniques, preferably by filtration.

It can optionally be subjected to a washing operation, for example using an alcohol, preferably methanol, ethanol or isopropanol.

Subsequently, as a result of the washing, the precipitate can be subjected to a drying operation which can be carried out in an oven under vacuum (reduced pressure generally between 20 and 100 mm of mercury) or under a stream of hot gas, for example air or nitrogen, at a temperature advantageously chosen between 60° C. and 110° C.

As mentioned above, the salification reaction is preferably carried out on the dihydroxybenzenedisulfonic acid resulting from the sulfonation stage.

Thus, the dihydroxybenzene corresponding to the dihydroxybenzenedisulfonic acid of formula (I) is subjected to a sulfonation operation which can be carried out with sulfuric acid or its oleums.

Recourse may be had to an aqueous sulfuric acid solution having a concentration of between 90 and 100%. It is preferable to employ a concentrated solution and, preferably, the 98% by weight commercial form is chosen.

Recourse may also be had to oleums, which correspond to sulfuric acid charged with sulfur trioxide $SO_3$, the concentration of which can vary between 10% and 65% by weight. Oleums comprising 20%, 40% or 60% by weight of $SO_3$ are commercially available.

The sulfonation is carried out in the presence of an excess of sulfuric acid.

The ratio of the number of moles of sulfuric acid to the number of moles of dihydroxybenzene is preferably at least 3 and more preferably between 4 and 6.

The sulfonation is in particular carried out at a temperature greater than the crystallization temperature of the reaction medium. It is preferably between 50° C. and 100° C.

In noncontinuous (batch) operation, the duration of the sulfonation reaction and, in continuous operation, the overall mean residence time are in particular between 1 and 10 h, more particularly between 1 and 5 h.

From a practical viewpoint, the dihydroxybenzene is generally introduced into the sulfuric acid and then heating is carried out at the chosen temperature.

The dihydroxybenzenedisulfonic acid is obtained in the presence of an excess of sulfuric acid, the ratio of the number of moles of sulfuric acid to the number of moles of dihydroxybenzenedisulfonic acid being greater than 1, preferably between 2 and 4.

At the end of the reaction, the reaction medium is diluted by addition of water in order to facilitate the stirring after salification.

The amount of water introduced is approximately 5 to 10 mol per mole of dihydroxybenzenedisulfonic acid.

It is preferable to minimize the amount of water involved.

Subsequently, the sulfate or hydrogen sulfate salt is introduced under the conditions described above.

At the end of the salification reaction, a reaction medium is obtained which has the essential characteristic of being highly concentrated in sulfuric acid.

Thus, the ratio by weight of the sulfuric acid to the metal dihydroxybenzenedisulfonate varies between 1 and 2.1 and preferably lies between 1.6 and 1.7.

Another characteristic of the reaction medium is that it comprises only a small amount of water.

Thus, the ratio by weight of the water to the metal dihydroxybenzenedisulfonate varies between 0.4 and 0.8.

Another characteristic is that only a small amount of metal sulfate is present.

The amount of metal sulfate formed is less than 5% of the weight of metal dihydroxybenzenedisulfonate obtained.

The precipitated metal dihydroxybenzenedisulfonate, which is preferably sodium dihydroxybenzenedisulfonate, is separated, preferably by filtration.

The process of the invention makes it possible to recover, subsequent to the separation operation, preferably by filtration, mother liquors having a high concentration of sulfuric acid of greater than 50% by weight, preferably between 60% and 65% by weight.

These mother liquors can be sent directly to the unit for the regeneration of the sulfuric acid, which is carried out in particular by conventional methods by incineration.

When the salification is carried out according to the process of the state of the art using sodium hydroxide, it is not possible to obtain mother liquors which are as concentrated due to the dilution contributed by the water formed during the reaction and the water contributed by the sodium hydroxide employed in the form of an aqueous solution.

Exemplary embodiments of the invention are given below by way of indication and without a limiting nature.

EXAMPLES

Example 1

682 g of 98% by weight sulfuric acid are charged to a 1 liter reactor and then 150 g of pyrocatechol are dissolved at ambient temperature.

The dissolution is exothermic (+40° C. approximately).

The reaction mass is then brought to 85° C.-90° C. for 5 hours in order to bring the sulfonation to completion.

After cooling to approximately 50° C., 221 g of water and then 371 g of potassium hydrogen sulfate are added to the reaction mass.

The potassium 1,2-dihydroxy-3,5-benzenedisulfonate formed precipitates from the reaction mass.

After cooling to approximately 15-20° C., the salt obtained is filtered off on a Büchner filter provided with a cotton cloth, then washed with 3 times 115 g of isopropanol and then dried under reduced pressure (50-60 mm of mercury) at 60° C.

403.3 g of potassium 1,2-dihydroxy-3,5-benzenedisulfonate are thus obtained, at 93.1% by high performance liquid chromatography (HPLC).

Mother liquors are collected, the sulfuric acid concentration of which is 74.5%.

The aqueous wash liquors are concentrated by heating (at approximately 110° C.) until the isopropanol is removed, and the residue obtained is mixed with the mother liquors.

This mixture, comprising approximately 651 g of sulfuric acid (more than 65%), can be regenerated to give 98% sulfuric acid and can be recycled to the synthesis.

Example 2

682 g of 98% by weight sulfuric acid are charged to a 1 liter reactor and then 150 g of pyrocatechol are dissolved at ambient temperature.

The dissolution is exothermic (+40° C. approximately).

The reaction mass is then brought to 85° C.-90° C. for 5 hours in order to bring the sulfonation to completion.

After cooling to approximately 50° C., 221 g of water and then 237.4 g of potassium sulfate are added to the reaction mass.

The potassium 1,2-dihydroxy-3,5-benzenedisulfonate formed precipitates from the reaction mass.

After cooling to approximately 15-20° C., the salt obtained is filtered off on a Büchner filter provided with a cotton cloth, washed with 3 times 115 g of isbpropanol and then dried under reduced pressure (50-60 mm of mercury) at 60° C.

404.6 g of potassium 1,2-dihydroxy-3,5-benzenedisulfonate are thus obtained, at 92.8% by HPLC.

Mother liquors are collected, the sulfuric acid concentration of which is 70.7%.

After concentrating the aqueous wash liquors, the residue is mixed with the mother liquors.

This mixture, comprising approximately 526 g of sulfuric acid (more than 61%), can be regenerated to give 98% sulfuric acid and can be recycled to the synthesis.

Example 3

682 g of 98% sulfuric acid are charged to a 1 liter reactor and then 150 g of pyrocatechol are dissolved at ambient temperature.

The dissolution is exothermic (+40° C. approximately).

The reaction mass is then brought to 85° C.-90° C. for 5 hours in order to bring the sulfonation to completion.

After cooling to approximately 50° C., 220 g of water and then 384.8 g of sodium hydrogen sulfate monohydrate are added to the reaction mass.

The sodium 1,2-dihydroxy-3,5-benzenedisulfonate formed precipitates from the reaction mass.

After cooling to approximately 15-20° C., the salt obtained is filtered off on a Büchner filter provided with a cotton cloth, washed with 3 times 115 g of isopropanol and then dried under reduced pressure (50-60 mm of mercury) at 60° C.

347.8 g of sodium 1,2-dihydroxy-3,5-benzenedisulfonate are thus obtained, at 93.6% by HPLC.

Mother liquors are collected, the sulfuric acid concentration of which is 68.2%.

After concentrating the aqueous wash liquors, the residue is mixed with the mother liquors.

This mixture, comprising approximately 657 g of sulfuric acid (more than 63%), can be regenerated to give 98% sulfuric acid and can be recycled to the synthesis.

Example 4

682 g of 98% sulfuric acid are charged to a 1 liter reactor and then 150 g of pyrocatechol are dissolved at ambient temperature.

The dissolution is exothermic (+40° C. approximately).

The reaction mass is then brought to 85° C.-90° C. for 5 hours in order to bring the sulfonation to completion.

After cooling to approximately 50° C., 220 g of water and then 227.6 g of sodium sulfate monohydrate are added to the reaction mass.

The sodium 1,2-dihydroxy-3,5-benzenedisulfonate formed precipitates from the reaction mass.

After cooling to approximately 15-20° C., the salt formed is filtered off on a Büchner filter provided with a cotton cloth, washed with 3 times 115 g of isopropanol and then dried under reduced pressure (50-60 mm of mercury) at 60° C.

365.4 g of sodium 1,2-dihydroxy-3,5-benzenedisulfonate are thus obtained, at 93.2% by HPLC.

Mother liquors are collected, the sulfuric acid concentration of which is 66.6%.

After concentrating the aqueous wash liquors, the residue is mixed with the mother liquors.

This mixture, comprising approximately 526 g of sulfuric acid (more than 59%), can be regenerated to give 98% sulfuric acid and can be recycled to the synthesis.

Comparative Example 5

In this example, Example 4 is repeated, except for the difference that the salification is carried out not using sodium sulfate but, as in the state of the art, using an aqueous sodium hydroxide solution.

682 g of 98% sulfuric acid are charged to a 1 liter reactor and then 150 g of pyrocatechol are dissolved at ambient temperature.

The dissolution is exothermic (+40° C. approximately).

The reaction mass is then brought to 85° C.-90° C. for 5 hours in order to bring the sulfonation to completion.

After cooling to approximately 50° C., 231.9 g of a 47% by weight aqueous sodium hydroxide solution are added to the reaction mass.

The sodium 1,2-dihydroxy-3,5-benzenedisulfonate formed precipitates from the reaction mass.

After cooling to approximately 15-20° C., the salt formed is filtered off on a Büchner filter provided with a cotton cloth, washed with 3 times 115 g of isopropanol and then dried under reduced pressure (50-60 mm of mercury) at 60° C.

340.7 g of sodium 1,2-dihydroxy-3,5-benzenedisulfonate are thus obtained, at 93% by HPLC.

Mother liquors are collected, the sulfuric acid concentration of which is 45.4%.

After concentrating the aqueous wash liquors, the residue is mixed with the mother liquors.

This mixture comprises approximately 400.4 g of sulfuric acid, which corresponds to a concentration of 46.6%.

Example 6

682 g of 98% sulfuric acid are charged to a 1 liter reactor and then 150 g of hydroquinone are dissolved at ambient temperature.

The dissolution is exothermic (+35° C. approximately).

The reaction mass is then brought to 85° C.-90° C. for 5 hours in order to bring the sulfonation to completion.

After cooling to approximately 50° C., 221 g of water and then 237.4 g of potassium sulfate are added to the reaction mass.

The potassium 1,4-dihydroxy-3,5-benzenedisulfonate formed precipitates from the reaction mass.

After cooling to approximately 15-20° C., the salt obtained is filtered off on a Büchner filter provided with a cotton cloth, washed with 3 times 115 g of ethanol and then dried under reduced pressure (50-60 mm of mercury) at 60° C.

392.9 g of potassium 1,4-dihydroxy-3,5-benzenedisulfonate are thus obtained, at 91.5% by HPLC.

After concentrating the aqueous wash liquors, the residue is mixed with the mother liquors.

This mixture, comprising approximately 528 g of sulfuric acid (more than 60%), can be regenerated to give 98% sulfuric acid, indeed can even be recycled to the synthesis.

What is claimed is:

1. A process for the preparation of a metal dihydroxybenzenedisulfonate from a corresponding dihydroxybenzenedisulfonic acid, comprising reacting the dihydroxybenzenedisulfonic acid present in a sulfuric medium, with a sufficient amount of a salt which comprises a sulfate or hydrogen sulfate anion.

2. The process as defined by claim 1, wherein the dihydroxybenzenedisulfonic acid corresponds to the following formula:

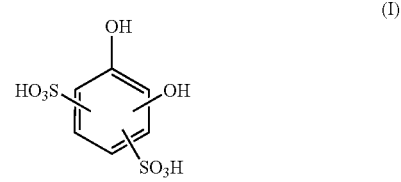

(I)

wherein:
the OH group is in the ortho, meta or para position with respect to the other hydroxyl group, and
the sulfonic $SO_3H$ groups are in the ortho and/or para position with respect to the hydroxyl groups.

3. The process as defined by claim 1, wherein said dihydroxybenzenedisulfonic acid is 1,2-dihydroxy-3,5-benzenedisulfonic acid, 1,3-dihydroxy-4,6-benzenedisulfonic acid or 1,4-dihydroxy-2,5-benzenedisulfonic acid.

4. The process as defined by claim 3, wherein said dihydroxybenzenedisulfonic acid is 1,2-dihydroxy-3,5-benzenedisulfonic acid.

5. The process as defined by claim 1, wherein the dihydroxybenzenedisulfonic acid is produced by sulfonation.

6. The process as defined by claim 2, wherein a dihydroxybenzene corresponding to the dihydroxybenzenedisulfonic acid of formula (I) is subjected to a sulfonation operation carried out with sulfuric acid or oleum thereof.

7. The process as defined by claim 6, wherein said sulfuric acid has a concentration of from 90% to 100% by weight or said oleum comprises from 10% to 65% by weight of sulfur trioxide.

8. The process as defined by claim 6, wherein the ratio of the number of moles of sulfuric acid to the number of moles of dihydroxybenzene is at least 3.

9. The process as defined by claim 5, wherein the sulfonation is carried out at a temperature of from 50° C. to 100° C.

10. The process as defined by claim 6, wherein the dihydroxybenzene is introduced into the sulfuric acid and then such medium is heated.

11. The process as defined by claim 1, wherein the medium of reaction is diluted with water and then stirred after salification.

12. The process as defined by claim 11, wherein the amount of water introduced is approximately 5 to 10 mol per mole of dihydroxybenzenedisulfonic acid.

13. The process as defined by claim 1, wherein the dihydroxybenzenedisulfonic acid is reacted with a sulfate or hydrogen sulfate of a metal element from Group Ia or Ib of the Periodic Table of the Elements.

14. The process as defined by claim 13, wherein the dihydroxybenzenedisulfonic acid is reacted with a sulfate or hydrogen sulfate of sodium or potassium.

15. The process as defined by claim 1, wherein the amount of sulfate or hydrogen sulfate salt, expressed by the ratio of the number of moles of sulfate or hydrogen sulfate salt to the number of moles of dihydroxybenzenedisulfonic acid, ranges from 1.6 to 2.5.

16. The process as defined by claim 1, wherein the sulfate or hydrogen sulfate salt is introduced into the reaction medium comprising the dihydroxybenzenedisulfonic acid and the temperature is adjusted to from 40° C. to 80° C.

17. The process as defined by claim 1, wherein the salt of the dihydroxybenzenedisulfonic acid is separated via solid/liquid separation technique.

18. The process as defined by claim 17, wherein the mother liquors resulting from the separation operation have a high concentration of sulfuric acid of greater than 50% by weight.

19. The process as defined by claim 18, wherein the mother liquors resulting from the separation operation are employed for the regeneration of sulfuric acid.

20. The process as defined by claim 1, wherein the salt of the dihydroxybenzenedisulfonic acid is subjected to a washing operation.

21. The process as defined by claim 1, wherein the salt of the dihydroxybenzenedisulfonic acid is subjected to a drying operation.

22. A reaction medium resulting from the salification stage of the process as defined by claim 1, having a ratio by weight of the sulfuric acid to the metal dihydroxybenzenedisulfonate ranging from 1 to 2.1 and wherein the ratio by weight of the water to the metal dihydroxybenzenedisulfonate ranges from 0.4 to 0.8.

23. The reaction medium as defined by claim 22, wherein the amount of metal sulfate formed is less than 5% of the weight of the product metal dihydroxybenzenedisulfonate.

24. A process for the preparation of a 1,2-dihydroxy-3,5-benzenedisulfonate of an alkali metal, comprising the following stages:

Introducing pyrocatechol into concentrated sulfuric acid or oleum thereof employed in an amount sufficient to produce the corresponding disulfonic acid, heating said medium at a temperature of from 50° C. to 100° C., introducing water in a minimum amount but an amount sufficient to render the medium stirrable after salification, reacting the dihydroxybenzenedisulfonic acid obtained with a sufficient amount of a sulfate or hydrogen sulfate of an alkali metal, and separating the 1,2-dihydroxy-3,5-benzenedisulfonate of an alkali metal obtained.

25. The process as defined by claim 24, wherein the alkali metal is sodium or potassium.

26. The process as defined by claim 15, wherein said ratio ranges from 1.9 to 2.1.

27. The process as defined by claim 26, wherein said ratio is about 2.0.

28. The process as defined by claim 1, wherein the quality of the metal dihydroxybenzenedisulfonate is not detrimentally affected.

\* \* \* \* \*